Figure 1:
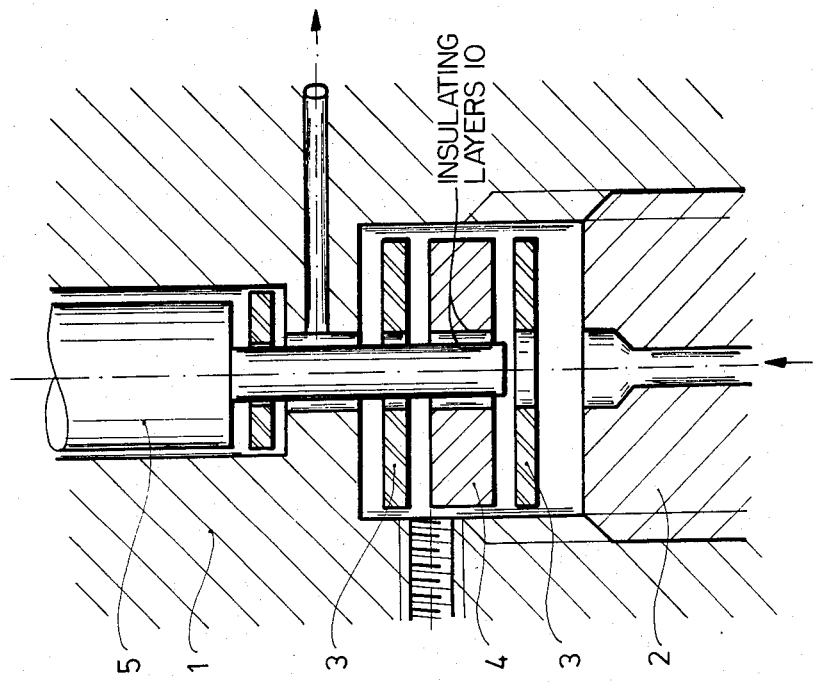

United States Patent [19]

Pungor et al.

[11] Patent Number: 4,634,982

[45] Date of Patent: Jan. 6, 1987

[54] CAPACITIVE MEASURING ELEMENT FOR OSCILLOMETRIC MEASUREMENT OF CONDUCTANCE OF STREAMING SOLUTIONS AND METHOD OF DETERMINING THE DIMENSIONS THEREOF

[75] Inventors: Ernö Pungor; Klára Tóth; Ferenc Pál; Béla Erös; József Nagy; László Bihátsi, all of Budapest, Hungary

[73] Assignee: Magyar Tudomanyos Akademia Kozponti Hivatals, Hungary

[21] Appl. No.: 531,784

[22] Filed: Sep. 13, 1983

[51] Int. Cl.$^4$ .................................. G01N 27/02
[52] U.S. Cl. ........................... 324/448; 324/447; 324/61 P
[58] Field of Search ............. 324/439, 442, 444, 448, 324/60 C, 450, 447, 446, 61 R, 61 P

[56] References Cited

U.S. PATENT DOCUMENTS 3,665,295  3/1972  Schoen .......................... 324/450

Primary Examiner—Reinhard J. Eisenzopf
Assistant Examiner—Jack B. Harvey
Attorney, Agent, or Firm—Sughrue, Mion, Zinn, Macpeak, and Seas

[57] ABSTRACT

The invention relates to a capacitive measuring element intended for continuous measurements of conductance in streaming solutions. The essence of the measuring element is that in the measuring space the surfaces limiting it are covered by an electrically insulating material. A method for obtaining the dimensions of the measuring element has also been proposed. According to the measuring element of the invention the measurements of concentration from very low values with high accuracy and low noise level are possible. The life duration and the reliability of the measuring element are high, and it shows a high resistivity against corrosive media to be measured.

10 Claims, 4 Drawing Figures

CAPACITIVE MEASURING ELEMENT FOR OSCILLOMETRIC MEASUREMENT OF CONDUCTANCE OF STREAMING SOLUTIONS AND METHOD OF DETERMINING THE DIMENSIONS THEREOF

The invention relates to the field of oscillometric measuring techniques and more exactly to a capacitive measuring element to be used in flow-through measuring techniques and to a method of determining the dimensions of the element. The proposed measuring element comprises a measuring electrode and a grounding electrode defining a measuring space of volume in 2 to 50 $\mu$l range. The measuring element according to the invention ensures the possibility of measurements of conductance in liquid media passing through the measuring space and thereby determining further physicochecmical parameters derived from conductance.

Different metering problems related to monitoring industrial processes and different scopes of chemical analysis require providing analysis of a great number of samples having similar composition. This requirement is present also in chromatographic investigations, and has promoted the elaboration of special methods of continuous measurements to be carried out in streaming liquid media. In the field of measurements realised in a stream of liquid one of the central problems is the selection of an appropriate measuring detector or measurement element for determining the features, or parameters of the liquid. A well-known type of measuring detector is the universal detector, the essence of which lies in oscillometric measurements of conductance (of high-frequency conductivity). The main requirements of this universal detector as a measuring element are small element volume, low threshold value for detection of concentration, high sensitivity and at least approximate linearity in a wide value range. In these universal detectors there is no galvanic contact between the liquid medium to be measured and the electrodes.

It is known, that conductometric detectors have already been used in liquid chromatography, wherein the liquid medium to be measured is in direct galvanic contact with the electrodes providing the measurement. A measuring element of this type is disclosed for example in the article of Svoboda, V. and Marsal, J. (J. Chromatograph., 148, 111, 1978) or of Poppe, H. and Kuyster, J. (J. Chromatogr. 132, 369, 1977). The galvanic contact causes a lot of problems, the most important of which are: the high threshold value of sensitivity, intensive corrosion of the surfaces and thereby low reproducibility, and high noise level.

The principle of the oscillographic measurements (high-frequency conductance), however, offers a possibility for measuring conductance and permittivity data of a liquid medium with a measuring element for chromatographic investigation in which the electrodes are not in galvanic contact with the medium to be measured passing through a space of small volume. The disadvantages present due to galvanic contact are obvious: the polarisation effect coming under the influence of the contact causes intensive corrosion of the metallic surfaces and thereby errors in the measurements, changes in the surface conditions of the electrodes, in the constants characterizing the measuring element, etc. There is no prior art known, which avoids the mentioned disadvantages in a measuring element of small volume, because the specialists skilled in the art were of the opinion that the principle of the oscillometric measurements may not be used due to the small volume. The literature discloses no measuring element for chromatographic measurements wherein the liquid medium to be measured is not in galvanic contact with the electrodes.

The present invention has the object of avoiding the known disadvantageous features of the known measuring elements having inner volume in a range of some microliters.

It is known that conductance K of a capacitive measuring element can be determined by the equation $$K = \frac{\omega^2 R C_s^2}{1 + \omega^2 R^2 (\epsilon C_{M,O} + C_s)^2} \qquad 1$$

wherein
 $\omega$ is the measuring frequency (usually in the range from 5 to 26 MHz),
 R is the resistance of the liquid medium to be measured,
 $C_s$ is the stray capacitance of the measuring element,
 $\epsilon$ is the permittivity of the liquid medium to be measured,
 $C_{M,O}$ is the measuring capacitance of the measuring element related to vacuum The product $\epsilon C_{M,O} = C_M$ means the measuring capacitance in case of measurements of a liquid medium of permittivity $\epsilon$.

The linearity of the answer given by the measuring element as it follows from the equation (1) can be reached in case of aqueous solutions if the value of the product in the denominator is less than one. In case of non-aqueous solutions the stray capacitance $C_s$ of the measuring element should be limited to a negligible level as compared to the measuring capacitance $C_M$, that means to about 1/10 part thereof. If the ratio of the mentioned capacitance is not higher the 0.1 then the denominator of the expression (1) comprises a negligibly low value of the stray capacitance $C_s$. In case of aqueous solutions the value of the resistance R is small and therefore the denominator of expression (1) can be considered as equal to unity. Thereby the expression $K = \omega^2 R C_s^2$ is given, which is a linear function of the resistance R, and thereby of the concentration at a stable value of frequency $\omega$. In case of non-aqueous solutions, however, the value of R is high and therefore in the denominator the product is much greater than one. Thereby the equation $$K = \frac{C_s^2}{R \epsilon^2 C_{M,O}^2} = k^{-1} \epsilon^{-2} \qquad 2$$

can be derived, wherein k is a constant.

Whether the above mentioned basic condition is satisfied can be proved on the basis of the expression (2). If the stray capacitance $C_s$ can really be neglected as compared to the measuring capacitance $C_M$ then the equation $\Delta(1/K) = k\Delta\epsilon^2$ should be satisfied by the values obtained by measurements of different liquid media of different permittivity values passing through the measuring space of measuring capacitance $C_M$, which media should be non-aqueous solutions of the same resistance values.

The invention has the object to make use of the above mentioned recognitions and thereby to provide a measuring element for use in chromatography, which can be characterized by very small inner volume and wherein a liquid medium can be measured at a very low noise level assuring the possibility of continuous oscillographic measurements of concentration from the lowest values.

In order to reach the object set a capacitive measuring element has been devised for oscillometric measurements of conductance in streaming solutions, comprising a measuring electrode and a grounding electrode in concentric arrangement defining a measuring space of volume in 2 to 50 µl range, wherein the measuring electrode and said grounding electrode are coated with an electrically insulating layer on their surfaces defining said measuring space, and the arrangement of said electrodes ensures a related to vacuum measuring capacitance at least as high as the stray capacitance of the element.

The life of the capacitive measuring element can be prolongated advantageously if the insulating layer consists of a material resistant to the streaming liquid media to be measured, for example of silicone resin or polymerized fluoric hydrocarbon.

In the measurements it is especially advantageous if in the measuring element the measuring electrode has a projection encircled by the grounding electrode. It can be also advantageous to shape the measuring electrode in form of a cylindrical ring, a frontal surface of which lies oppositely to the grounding electrode.

It has been elaborated a method of dimensioning a capacitive measuring element for oscillometric measurements in streaming solutions, whereby in a body a measuring electrode and a grounding electrode are concentrically arranged and thereby a measuring space is defined, through the measuring space non-aqueous solutions of at least approximatively identical resistance are passed, wherein the permittivity values $\epsilon$ of the solutions are different, and the further steps are performed: measuring conductance K of each solution, checking on the basis of the measured values whether they satisfy at least approximately the equation $\Delta(1/K)=k\Delta\epsilon^2$, wherein k is a constant, further if the measured values differ from the values following from this relation changing at least one of the parameters characterizing the relative position and dimensions of the measuring electrode and grounding electrode arranged concentrically, and performing the measurements of conductance and if the equation is satisfied determining the dimensions of the electrodes in the body, and of the body and identifying them with the dimensions of the measuring element.

As characteristic parameter it is advantageous to choose the magnitude and/or the distance of the surfaces lying oppositely to one another in the measuring space.

The capacitive measuring element as invented ensures the possibility of measuring conductance of liquid media streaming through a measuring space with volume in range from 2 to 50 µl, which is desirable in chromatography, wherein a very low noise level can be reached, and the measurements can be provided continuously. The values obtained by continuous oscillometric measurement make possible the definition of a lot of other values if they can be derived from conductance.

Figure 2:
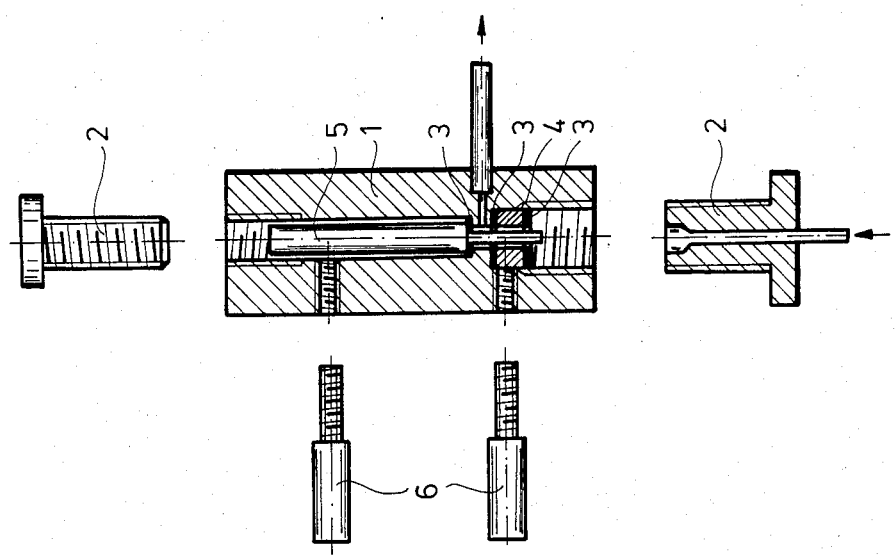
Figure 3:
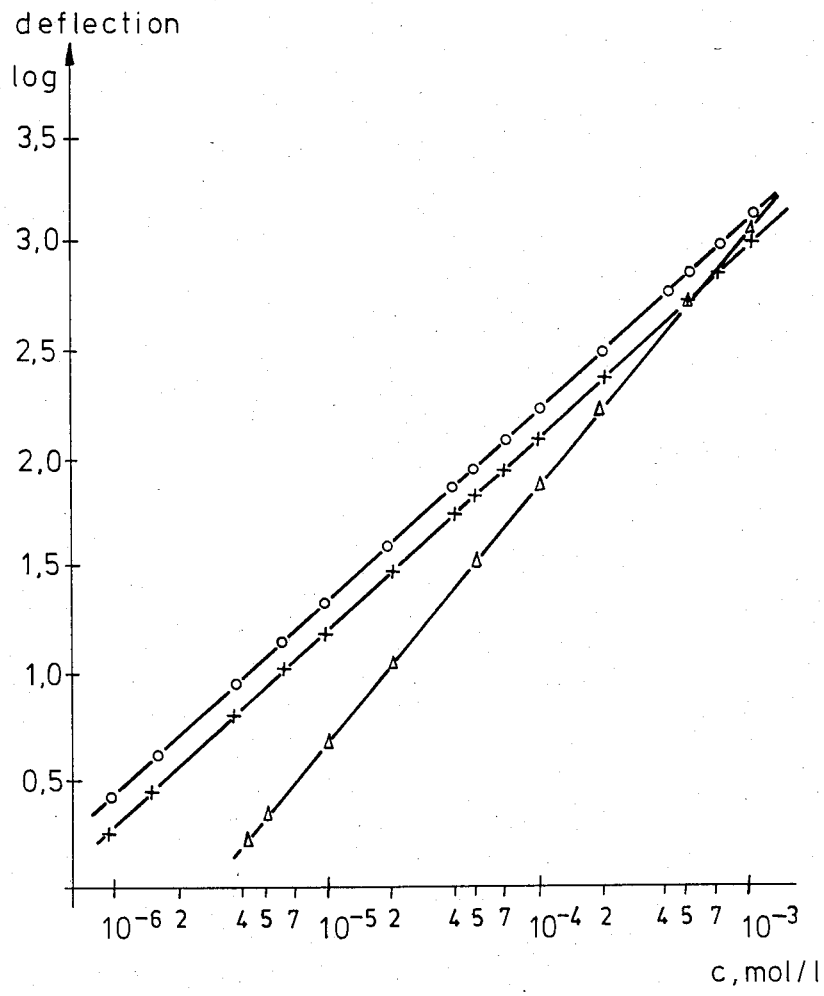
Figure 4:
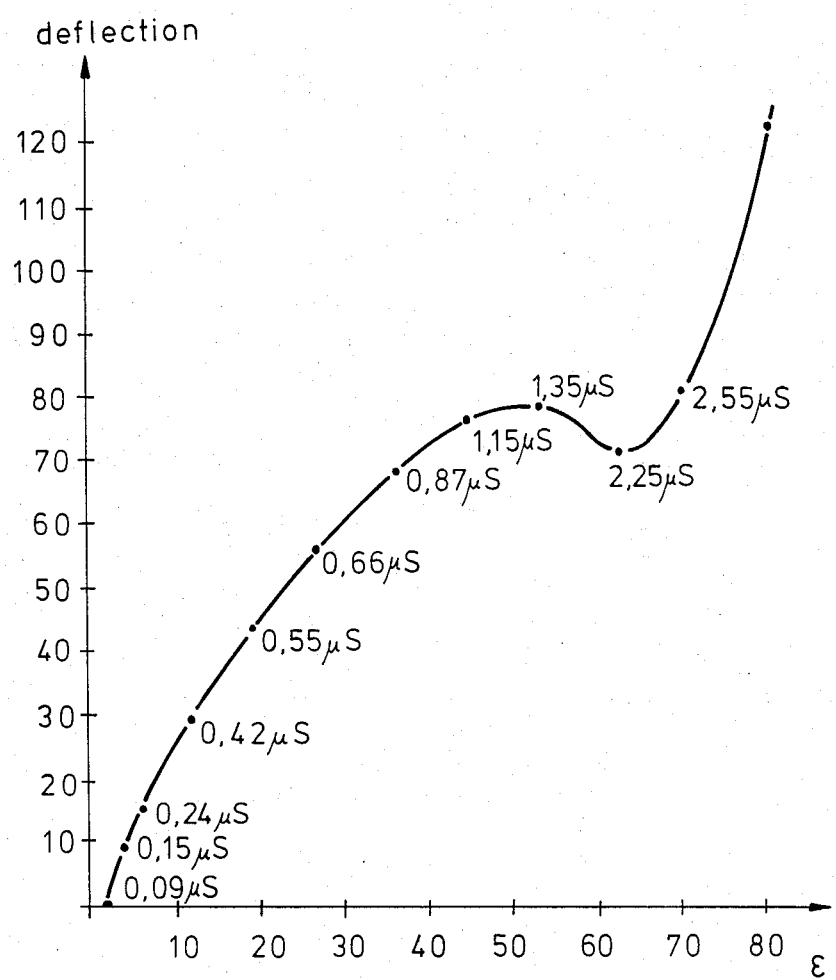

Further objects and features of the invention will be better understood in accordance with the attached drawings. In the drawings:

FIG. 1 shows a cross-section of a capacitive measuring element constructed according to the invention, FIG. 2 is a cross-section of a fragmentary part of the capacitive measuring element according to the invention, FIG. 3 shows some calibration curves for aqueous solution of KCl and FIG. 4 shows some calibration curves for non-aqueous solutions prepared in form of dioxane-water mixtures of different conductance values.

The capacitive measuring element according to the present invention (FIGS. 1 and 2) comprises a pipe-shaped body 1 through which there is an inner opening closed from both side by fixing screws 2 one of which comprises an inner opening. In the body 1 there are a measuring electrode 5, and a grounding electrode 4 connected both to respective screws 2. The grounding electrode 4 is shaped in the form of a ring, and is separated from the corresponding fixing screw 2 by means of a sealing ring element 2 which is arranged concentrically and is made of polytetrafluorethylene. The liquid medium can flow through the inner space of the concentrically arranged sealing rings 3 and grounding electrode 4. Both the grounding electrode 4 and the measuring electrode 5 are connected to outlets 6. The measuring electrode 5 is supported in the body 1 by means of sealing rings 3 made of polytetrafluoroethylene, and is advantageously shaped with a projection which lies at least partly in the inner space of the grounding electrode 4. It can be advantageous to shape it in a form, when the grounding electrode 4 has a flange and thereby is supported on the body 1, wherein the frontal face of the ring shaped measuring electrode 5 and the opposite surface of the grounding electrode 4 are covered by a layer 10 made of electrically insulating material. In this way the measuring electrode 5 and the grounding electrode 4 are arranged opposite to one another and the surfaces are small.

The essence of the invention lies in that the surfaces of the measuring electrode 5 and grounding electrode 4 which define a measuring space of volume in range from 2 to 50 µl are covered with an electrically insulating layer 10. As experience shows the electrically insulating layer is advantageously a silicone resin prepared by burning in or polytetrafluoroethylene (or other polymerized fluorohydrocarbon) prepared by the usual technological steps. During the measurements these materials had the most favorable characteristics.

When constructing and using the proposed measuring element the steps are the following.

In concentrical arrangement of the grounding electrode 4 and the measuring electrode 5 their dimensions and relative position (distance and magnitude of the surfaces lying oppositely to one another) should be changed in possibly little steps. This means for example that the height of the ring-shaped grounding electrode 4, the length of the projection of the measuring electrode, the thickness of the insulating layer covering the electrodes, the width of the ring-shaped space formed by the electrodes therebetween. It can be advantageous also to modify the thickness of the metallic part of the electrodes, however, always the concentrical arrangement of the grounding electrode 4 and the measuring electrode 5 should be ensured. For all possible arrangements the equation (2) has to be controlled. For this aim, as described above, solutions of high identical resistance R, but of different permittivity should be passed through the inner space of the measuring element. If the measured values satisfy the mentioned equation $\Delta(1/K)=k\Delta\epsilon^2$, the dimensions of the measuring element have to be determined and the measuring element can be used as sample.

When using the measuring element according to the invention calibration curves are to be determined (FIGS. 3 and 4) for aqueous and non-aqueous solutions in order to determine the constants characterizing the measuring element. As follows from FIG. 3 in case of aqueous solutions the values are very advantageous because the concentration can be measured down to $10^{-6}$ mol/l and the answers are linear up to about $10^{-3}$ mol/l. In case of non-aqueous solutions the values of conductivity and permittivity can be assigned to one another on basis of the calibration curves and if required, the values should be determined by interpolation. The calibration curve of FIG. 4 relates to a water-dioxane mixture and it shows the different values of conductance relating to different permittivity along the curve of swing of a pointer.

The following data were measured which verify the advantageous features of the measuring element according to the invention:

| Measuring volume, $\mu$l | concentration, mol/l | Threshold value of detection of material quantity, ng |
|---|---|---|
| 12.0 | $2.0 \times 10^{-6}$ | 1.8 |
| 19.5 | $1.5 \times 10^{-6}$ | 2.2 |
| 39.0 | $1.6 \times 10^{-6}$ | 4.7 |

The measuring element according to the invention makes possible the measurements of very low values of concentration with high accuracy, with low noise level. The life of the measuring element is high, the reliability is also high, and it is in high degree resistive against the corrosive solutions to be measured.

We claim:

1. Capacitive measuring element for oscillometric measurement of streaming solutions by flow-through measuring techniques, comprising a measuring electrode and a grounding electrode disposed around said measuring electrode in a concentric arrangement defining a measuring space having a volume in a range of 2 to 50 $\mu$l, further comprising an electric insulating layer which coats respective surfaces of said measuring electrode and said grounding electrode defining said measuring space, said electrodes being arranged to ensure a measuring capacitance relative to vacuum at least as high as their stray capacitance, whereby both conductivity and permittivity of said streaming solutions may be measured.

2. Capacitive measuring element according to claim 1, wherein the insulating layer comprises material resistant to the streaming solution to be measured.

3. Capacitive measuring element according to claim 1, wherein the insulating layer comprises silicone resin.

4. Capacitive measuring element according to claim 1, wherein said insulating layer comprises polymeric fluoric hydrocarbon, such as polytetraflouroethylene.

5. Capacitive measuring element according to claim 1, wherein said measuring electrode comprises a projection encircled by said grounding electrode.

6. Capacitive measuring element according to claim 1, wherein said measuring electrode is shaped in form of a cylindrical ring wherein said grounding electrode lies opposite a frontal face of the ring.

7. Method of defining dimensions of a capacitive measuring element for oscillometric measurement of streaming solutions, comprising the steps of
   (a) arranging a grounding electrode concentrically around a measuring electrode in a body as to define a measuring space between said grounding electrode and said measuring electrode having a volume in a range of 2 to 50 $\mu$l,
   (b) passing through said measuring space different non-aqueous solutions of approximately identical resistance and of different permittivity ($\epsilon$),
   (c) measuring a conductance (K) of each solution,
   (d) controlling on the basis of the measured values whether they at least approximate the relation $(1/K) = k\epsilon^2$, wherein k is a constant,
   (e) if the measured values differ from that satisfying the relation, changing at least one of parameters characterizing the relative position and dimensions of said measuring electrode and grounding electrode arranged concentrically, and performing said steps (c)–(d), and
   (f) if the relation is satisfied, determining the dimensions and
   (g) identifying them with the dimensions of the measuring element.

8. A method according to claim 7, wherein total surface area of the respective opposing surfaces of said measuring electrode and said grounding electrode is changed.

9. Method according to claim 7, wherein the distance between respective opposing surfaces of said measuring electrode and said grounding electrode is changed.

10. Capacitive measuring element for flow-through measurements in streaming liquid media, comprising a measuring electrode and a grounding electrode concentrically positioned around said measuring electrode, said electrodes being positioned between an inlet and an outlet of said element and defining a measuring space having a volume in a range of 2 to 50 $\mu$l and limited by walls made of insulating material coating said electrodes and connected to said inlet and outlet, wherein said electrodes being arranged in a system having a capacitance relative to vacuum at least as high as its stray capacitance, whereby conductivity measurements in both aqueous and non-aqueous solutions may be carried out.

* * * * *